US011154227B2

(12) United States Patent
Benford

(10) Patent No.: US 11,154,227 B2
(45) Date of Patent: Oct. 26, 2021

(54) PORTABLE NEUROCOGNITIVE ASSESSMENT AND EVALUATION SYSTEM

(71) Applicant: Jacob Benford, Aptos, CA (US)

(72) Inventor: Jacob Benford, Aptos, CA (US)

(73) Assignee: HHITT, INC., Aptos, CA (US)

( * ) Notice: Subject to any disclaimer, the term of this patent is extended or adjusted under 35 U.S.C. 154(b) by 262 days.

(21) Appl. No.: 16/362,049

(22) Filed: Mar. 22, 2019

(65) Prior Publication Data

US 2019/0216381 A1 Jul. 18, 2019

Related U.S. Application Data

(63) Continuation of application No. 13/422,125, filed on Mar. 16, 2012, now abandoned.

(60) Provisional application No. 61/454,287, filed on Mar. 18, 2011.

(51) Int. Cl.
*G09B 5/02* (2006.01)
*A61B 5/16* (2006.01)
*G09B 5/00* (2006.01)

(52) U.S. Cl.
CPC ............. *A61B 5/162* (2013.01); *A61B 5/165* (2013.01); *A61B 5/168* (2013.01); *G09B 5/00* (2013.01); *G09B 5/02* (2013.01)

(58) Field of Classification Search
None
See application file for complete search history.

(56) References Cited

U.S. PATENT DOCUMENTS

| 2009/0017880 A1* | 1/2009 | Moore | H04M 1/72403 |
| | | | 455/575.1 |
| 2013/0023747 A1* | 1/2013 | Karo | A61B 5/4872 |
| | | | 600/384 |

* cited by examiner

*Primary Examiner* — James B Hull
(74) *Attorney, Agent, or Firm* — Donald R. Boys; Central Coast Patent Agency LLC

(57) ABSTRACT

A physical and cognitive field-testing apparatus has a substantially planar touchscreen display on one surface, facing on one direction, and a second display facing in an opposite direction, Internet communication functionality with at least one Internet-based computerized server, a local processor and on-board digital memory, and first software executing on the local processor, an interactive window displayed on the touchscreen display as a result of the display data, comprising at least two graphic artifacts, visually associated with at least a balancing test and a coordination test, an accelerometer installed on the portable computerized appliance, at least two graphic artifacts, at least one of which is associated with the accelerometer.

10 Claims, 14 Drawing Sheets

PORTABLE NEUROCOGNITIVE ASSESSMENT AND EVALUATION SYSTEM

CROSS-REFERENCE TO RELATED DOCUMENTS

The instant application is a continuation of co-pending U.S. application Ser. No. 13/422,125 which claims priority to U.S. provisional application Ser. No. 61/454,287, filed Mar. 18, 2011, entitled "Diagnosis of Acute Concussion Using Handheld Electronic Device". Priority is claimed to both parent applications, and the entire disclosure of both parent applications id incorporated at least by reference.

BACKGROUND OF THE INVENTION

1. Field of the Invention

The present invention relates generally to a computerized testing system for assessment of cognitive status and pertains more particularly to a neurocognitive and psychomotor performance assessment and evaluation system for use in a portable hand-held computerized device.

2. Discussion of the State of the Art

In the field of human neurocognitive psychomotor performance assessment and evaluation, testing systems are used in a wide range of situations which produce changes in brain function. Such testing may be employed in the evaluation of persons who have or are experiencing stroke, various disease conditions, exposure to toxic chemicals, rapid decompression, jet lag and so on. In the field of sports, particularly contact and even non-contact sports, such testing is particularly valuable for evaluating persons who have been subjected to sports injuries, particularly those involving direct or indirect impulsive force to the head, wherein various levels of concussion may exist. In such cases it is very important to implement post-injury neurocognitive and psychomotor performance testing in order to determine if a concussion exists, and if so, the level of concussion to ensure the safety of the injured player and/or determine if a player may return to the field, etc.

The study of the effects of concussions on cognitive and physical performance is a fairly new area of concentration that is gaining rapid attention because it is estimated in the fields of health care and clinical research that a majority of head traumas are attributed to concussions, few of those requiring hospital treatment. A concussion has been defined as any hit or blow to the head resulting in a neuropsychological change in the brain. While neurocognitive functioning can be altered for a few seconds, it also can be altered for the rest of one's life. The difference in these two situations, and anything in between, is that concussions have different levels of severity. Depending on several factors such as the severity of the direct or indirect impulsive force to the head for example, whether or not such force was repeated and if so, how many times, and whether or not there was lack of consciousness (and if so for how long) helps determine the severity of the concussion.

Symptoms of concussion include but are not limited to headache, disorientation, dizziness, nausea, vomiting, slurred or incoherent speech, lack of balance and coordination, emotional outbursts, short and long term memory loss, loss of consciousness, and light/sound sensitivity. When in some cases only a few of these symptoms are present after a blow to the head, for example, it may sometimes be difficult to determine whether or not a concussion actually occurred, or if these symptoms are simply the result of an initial shock to the head. In the field of neurocognitive performance assessment and evaluation, different levels of concussion have been set to explain the differences within concussions.

Traditionally concussions were categorized. A first category is severe concussion which has been defined as a combination of three or more of the aforementioned symptoms, in addition to loss of consciousness for a period greater than five minutes, as well as post traumatic amnesia for a period of up to twenty-four hours. In situations such as this, advanced medical care is required. A second category is a mild concussion. As with severe concussion, a mild concussion includes at least three or more of the above stated symptoms as well as loss of consciousness and amnesia, but the duration of both is shorter; loss of consciousness for less than five minutes, and less than thirty minutes of post traumatic amnesia. A third category is an acute concussion. As with severe and mild concussions, an acute concussion meet three or more of the above stated symptoms, but there is no loss of consciousness and there may or may not be amnesia. If amnesia does exist, the duration is less than thirty minutes. While acute concussions are far less dangerous than severe or mild concussions, there is still the possibility of the occurrence of post-injury cognitive functioning. Now concussions are thought of more on a continuum, based on symptoms and length of recovery.

Acute concussions are the most common type of concussion, particularly in sports wherein player-to-player or player-to-object contact is possible. Because some of the symptoms at this level of concussion last for a relatively short period of time, and there is no loss of consciousness and amnesia may or may not exist, this type of concussion may easily go unnoticed, and is also the most difficult to diagnose, particularly in the field.

In current art the diagnosis of acute concussion is performed using evaluation of symptoms, verbal questions, physical and cognitive performance measures, and even a pen-and-paper type assessment tool. In the present state of the art, evaluation and initial diagnosis of persons that have a known or suspected concussion or mild traumatic brain injury (MTBI) is commonly performed in physician/clinician offices using a written assessment tool which is a paper form comprising a series of questions and listed symptoms requiring largely Y/N indications which equate to a total "scoring". The resulting information is evaluated by skilled artisans in the office to enable conclusion of an initial evaluation and diagnosis. A common written test of this type is known as the Acute Concussion Evaluation (ACE) test form which is part of the "Heads Up: Brain Injury in Your Practice" tool kit developed by the Centers for Disease Control and Prevention (CDC). The ACE form was developed to provide physicians or other skilled practitioners with an evidence-based protocol to conduct an initial evaluation and diagnosis, as well as to serially track symptom recovery over time. Other such test forms are widely used in this field of endeavor.

Although such written tests may be of some value in the assessment of symptoms for aiding a trained artisan such as a neuropsychologist in an initial diagnosis of acute concussion or other MTBI as well as tracking symptom recovery, they offer only limited information providing at best only enough information to enable initial screening of persons that have a known or suspected concussion or MTBI. Such written tests are cumbersome and time consuming and have little value when a speedy determination of a person's neurocognitive fitness is required, and no value when it comes to psychomotor performance evaluation, particularly when involving an injured sports player that is needed back out on the field to continue play if it is safe for him/her to do so. Further, many of the symptoms of acute concussion are shared with many other conditions which may impair a person's neurocognitive performance, such as depression, under the influence of substances that alter mind, mood or motor skills, as well as a variety of other medical conditions. Still further, brain injuries do not always occur when neuropsychologists or other skilled administrators are nearby, and symptoms of acute concussion often resolve before the brain has completely recovered.

The sheer numbers of brain injuries, particularly concussions, have inclined the use of computerized neurocognitive testing (CNT) for the assessment of post-injury cognitive status, particularly when further medical attention is required. Several such computer programs exist that perform neuropsychological testing on patients after they sustain a concussion to help medical providers and practitioners determine when a patient has completely recovered and is able to safely return to normal activities. Presently, such test systems are available only on costly, full-featured desktop or notebook computers, and are administered in an environment conducive to such testing which, in the case of sports-related injuries, is typically far removed from the field location where the injury occurred. Administrators of such computerized testing may include athletic directors or trainers, school nurses, team doctors or the like, and typically must have completed extensive training in the administration of the test. The cost and physical size of such computerized testing systems render their use impractical in many situations; particularly, for on-the-spot evaluation of injured team players on the field. In many cases an injury to a player may at first appear to be an acute concussion, but if a concussion does not exist it may be desirable for the player to return to the field and resume play when able to do so as soon as possible. Such large computerized systems do not provide the capability of immediate on-the-spot diagnosis of acute concussion.

CNT systems are available today for use in some smaller computing devices but such systems simply move the pen and paper type testing, evaluation, tracking and test batteries and modules that exist today on larger computer platforms, to a portable computing platform. Such systems remain particularly deficient in providing all of the comprehensive testing useful in objectively but accurately determining the true state of a person's neurocognitive and psychomotor performance fitness, particularly in such areas as balance, coordination, eye tracking and so on.

Therefore, a need clearly remains for a simple, low-cost, portable and flexible computerized human neurocognitive and psychomotor performance testing and evaluation tool which would aid medical professionals or other qualified administrators in quickly and determinately diagnosing acute concussions while in or near the field location of an injury to an individual suspected of sustaining a concussion, either due to a witnessed injury or an individual's display of possible acute concussion symptoms. Such a system would provide all of the cognitive and physical performance test batteries to enable a person of ordinary skill in the art to more conclusively make a decision, while near or at the injury field location, as to whether or not an acute concussion exists, and generate point-of-use reporting which could provide immediate comparisons with normative data and/or to the injured person's past test performance so that timely, accurate and appropriate actions can be taken based on the test results. Such a system would be simple and low-cost, provide software applications that are downloadable and installable on a widely available low-cost handheld computing platform device, and a plurality of the devices could be interconnected over a wide area network such as the Internet to enable inter-device data sharing as well as that between field and host devices and central mass data storage. If an acute concussion is determinate, subsequent retesting once the patient has fully recovered can be performed to determine if the injured party had returned to either pre-injury performance or predefined age/sex specific norms, whereby the injured party could return safely to the field activity.

BRIEF SUMMARY OF THE INVENTION

In one embodiment of the invention a neurocognitive assessment and evaluation system is provided, comprising a portable computerized appliance having a touchscreen, network communication functionality, at least one processor and on-board digital memory, and software executing on the at least one processor. The software provides an interactive display comprising one or more graphics artifacts with which a person may interact, monitoring of the time and nature of the person's interaction with the one or more graphics artifacts, and audio or text instruction for the person to follow to interact with the one or more graphics artifacts to perform a specific test for neurocognitive evaluation of the person.

Also, in one embodiment the software first provides a plurality of icons displayed to represent different specific tests, and upon selection of an icon, the software causes specific graphics artifacts associated with the selected test to be displayed along with text or audio instruction for the person to interact with the displayed one or more graphics artifacts to perform the selected test.

Further in one embodiment the interactive display further comprises a toolbox area with interactive icons for initiating specific tools, utility or navigation functions. In some embodiments icons are provided to initiate a home navigation to a main menu, an icon for viewing and editing specific data associated with tested persons, undo and redo functions, and an icon for accessing configuration functions.

In specific embodiments one or more functions are provided by the software for communicating with one or more network-based servers, which may be used for downloading new or revised tests from the one or more network-based servers, or for uploading text results and test subject identity to the one or more network-based servers.

In one embodiment the system further comprises an accelerometer, and one of the specific tests is for testing a subject's balancing ability by providing two graphics artifacts, one of which moves on the screen relative to the movement of the device as sensed by the accelerometer, and the other of which remains stationary on the screen.

In one embodiment one of the specific tests assesses the person's reaction time by presenting or manipulating a graphics object at a first time and recording an action by the person at a second time in response to seeing the presentation at the first time. In this and other embodiments one of the specific tests assesses the person's coordination by presenting moving graphics objects and tracking a person's interaction with the moving graphics objects. In yet other embodiments there may be a specific test to assess recollection by presenting graphics objects in a series and measuring the person's ability to recall whether newly presented objects were presented before in the same test.

Other specific tests are provided in other embodiments, such as one to measure the person's number sequence memory by presenting a sequence, and then asking the person to repeat the sequence sometime after the presented sequence has been deleted from the screen, another to measure pattern recognition by presenting a pattern and asking the person to repeat the pattern or select the same pattern in a subsequent display, another to measure color recognition by presenting color words in a font color, and asking the person to signal when the text word and the color match.

Other tests provided are measuring impulse sensitivity by displaying series of graphics artifacts designed to cause the person to react impulsively, measuring problem solving ability by presenting graphics artifacts in a manner to create a problem, and asking the person to perform an act which solves the problem, including an image capturing device in the system, and eye movement and coordination by presenting specific graphics artifacts, asking the person to watch the artifacts as they move, and tracking the image capturing device the movement of the person's eye or eyes, and measuring memory function by presenting character sequences, erasing the character sequences, and then asking the person to enter the character sequences using an input function.

In another aspect of the invention a method for performing neurocognitive assessment and evaluation of a person is provided, comprising the steps of (a) providing on a portable computerized appliance having a touchscreen, network communication functionality, at least one processor and on-board digital memory, with software executing on the at least one processor; (b) providing on the touchscreen audio or text instruction for the person to follow to interact with the one or more graphics artifacts to perform a specific test for neurocognitive evaluation of the person; (c) displaying by the software one or more graphics artifacts with which a person may interact; and (d) monitoring the time and nature of the person's interaction with the one or more graphics artifacts.

In some cases of the method the software first provides a plurality of icons displayed to represent different specific tests, and upon selection of an icon, the software causes specific graphics artifacts associated with the selected test to be displayed along with text or audio instruction for the person to interact with the displayed one or more graphics artifacts to perform the selected test.

BRIEF DESCRIPTION OF THE SEVERAL VIEWS OF THE DRAWINGS

The present invention will be better understood from the following detailed description of a preferred embodiment of the invention, taken in conjunction with the accompanying drawings in which like reference numerals refer to like parts and in which.

DETAILED DESCRIPTION OF THE INVENTION

The present invention pertains to a computerized testing system for assessment and evaluation of human cognitive status, and pertains more particularly to a neurocognitive and psychomotor performance assessment and evaluation system for use in a portable hand-held computerized device, enabling administration of a series of tests provided by software components executed by the handheld device. In a preferred embodiment of the invention the series of tests provided by the system can be utilized to quickly, objectively and determinately diagnose whether or not the condition of acute concussion exists as a result of a witnessed injury or an individual's display of possible acute concussion symptoms. The flexible and portable nature of the invention enables on-the-spot administration of the test series while the administrator is in or near the field location of an injury, in order to make a decision as to whether the injured individual is safe to return to the activity during which the injury occurred, or discontinue the activity and possibly seek further medical attention.

Figure 1:
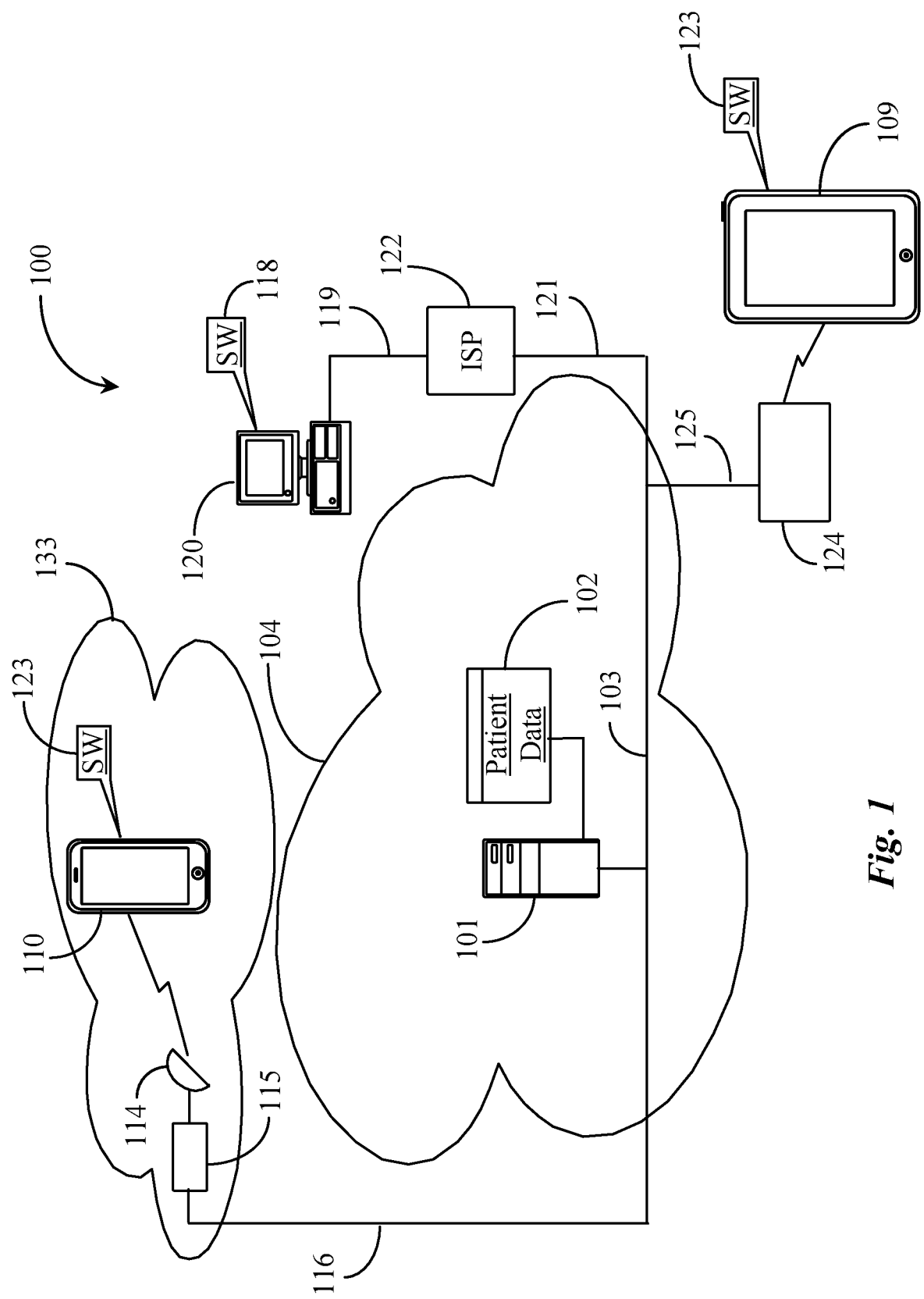
FIG. 1 illustrates an exemplary architectural diagram of a network-based system which may be used to implement a neurocognitive and psychomotor performance evaluation and testing system according to the preferred embodiment of the present invention.

FIG. 1 architecturally illustrates a basic system configuration in which the present invention may be implemented in accordance with a preferred embodiment of the present invention. In the following detailed description of embodiments of the present invention numerous specific details are set forth in order to provide a thorough understanding of the present invention. However, it will be apparent to those skilled in the art that the present invention may be practiced without all of these specific details. In other instances, well-known methods, procedures and components are not described in detail in order to avoid unnecessarily obscuring the new and novel aspects of the invention.

System 100 is a networked computerized system in which a neurocognitive and psychomotor performance evaluation and testing system designed for use on a portable, handheld computing platform may be implemented. System 100 generally includes an Intranet/Internet network represented by cloud 104, and a wireless cellular network represented by cloud 133. The aforementioned communications networks support communications between pluralities of diverse terminal devices as illustrated by computing devices represented by tablet device 109, cellular phone device 110 and computer 120. All of these networked devices as represented in the illustration can be either a single or plurality of geographically disparate devices without departing from the scope and spirit of the invention.

Line 103 represents all of the interconnecting structure and packet-routing capability in the Internet. Server 101 is an Internet-connected server hosted by an Internet Service Provider (ISP) providing Internet connection services according to systems well known in the art. In practice, server 101 may be a single server or group of servers providing specific services in the invention, and the plurality of servers may or may not be geographically common. Server 101 is coupled to a data repository 102 which stores data pertaining to subscribed users, including authorization and other specific information pertaining to administrators, patients and so on. Such data will be described further in the specification.

The communications system of FIG. 1 illustrates a device 109, capable of accessing services and information provided by Internet server 101 through wireless network 124 connected to Internet backbone 103 by connection line 125. Device 109 represents one or a plurality of devices which in a preferred embodiment of the invention is a mobile computer, larger than a mobile phone or personal digital assistant (PDA), but smaller than a laptop or most notebook computers and integrated into a flat touch screen. Such devices are well known in the art as tablet personal computers, having more advanced computing ability and connectivity than a simpler mobile phone or PDA, and the ability to execute various proprietary or third-party software applications. SW 123 is an application executable by device 109, providing functionality for neurocognitive and psychomotor performance evaluation, testing and diagnosis of acute concussion or other MTBI. SW 123 is a downloadable software application which may be installed on device 109 via any known means including a person or host computer, or possibly another handheld computing device. SW 123 is an executive program comprising an interactive interface and includes various modules including a battery of different cognitive testing and evaluation components, including physical balance and performance measures, as well as data-accessing modules for test result interpretation, registration, reporting and supporting utilities.

Device 109 comprises many of the features of a modern tablet computer such as touch user interface with perhaps multi-touch capabilities and concurrently capacitive or resistive touch screen, digital still and video camera, media player, web browser, and high-speed data access via Wi-Fi and mobile broadband. In a preferred embodiment device 109 also features an accelerometer function which detects the physical movement of the device itself, and can also be used to detect the orientation of the device relative to the center of the earth. More on the specific application of this feature in practicing the invention will be discussed later in the specification. Examples of such modern tablet computers may include Apple, Inc.'s iPad™ or Samsung's Galaxy Tab™. However, it is important to note that not all of the aforementioned features which are typically found in modern tablet computers are required to practice all of the unique and advantageous aspects of the invention. Of further importance to note is that although in a preferred embodiment of the invention the system utilizes a portable computing platform represented by device 109 which is such as the iPad™ or Tab™ device, other like devices may also be utilized without departing from the spirit of the invention, provided that such devices comprise, or are capable of being enhanced with features that can support the software functionality provided by the system of the invention such as SW 123, as will be described later in the specification it further detail. Such devices may include but are not limited to personal digital assistant (PDA), small notebook computers, or any other tablet-sized personal computing device comprising an operating system (OS) capable of supporting such hardware/software features as described above for device 109.

System 100 also comprises a wireless cellular network 133 comprising one or a plurality of cellular communication devices represented by cellular device 110, a network of base stations represented by element 114 and a cellular service 115 which acts as a gateway to the Internet via line 116. Device 110 in a preferred embodiment is a mobile phone built on a computing platform, well known in the art as a Smartphone, having more advanced computing capability and connectivity than a simpler feature phone, and the ability to execute various proprietary or third-party software applications. Device 110 comprises many of the features of a modern Smartphone including digital and video camera, high-resolution touch screen display, media player, web browser, and high-speed data access via Wi-Fi and mobile broadband. In a preferred embodiment device 110 also features an accelerometer function which detects the physical movement of the phone itself. Examples of such modern smartphones may include Apple, Inc.'s iPhone™ or Google's Galaxy Nexus™ using the Android™ OS. However, it is important to note that not all of the aforementioned features which are typically found in modern smartphones are required to practice all of the unique and advantageous aspects of the invention. Of further importance to note is that although in a preferred embodiment of the invention the system utilizes a Smartphone represented by device 110 which is such as the iPhone™ or Nexus™ device, other like devices may also be utilized without departing from the spirit of the invention, provided that such devices possess, or are capable of being enhanced with features that can support the software functionality provided by the system of the invention. Device 110 also executes an instance of software SW 123 which is downloadable to, and executable by device 110 and which may be installed on device 110 via any other known means. It is the unique and advantageous capability, and the portable nature of this capability that is at the heart of applicant's invention. Many more specific details of SW 123 functionality will be disclosed further in the specification.

System 100 also comprises computer 120 representing one or a plurality of individual computers which could be desktop or laptop computers for example. Computer 120 in capable of interacting with and accessing services and data provided by server 101 through Internet Service Providers (ISP) 122 via connection line 119 between computer 120 and ISP 122, and line 121 between ISPs 122 and Internet backbone 103. It should be understood that computer 120 may represent any home-based or business-based computer that can be Internet-connected utilizing any known connection means without departing from the scope and spirit of the invention. Computer 120 therefore is enabled with inherent Internet connection software, and in an embodiment of the invention also executes an instance of SW 118, which in an embodiment of the invention is a stand-alone software program, or a module of SW 123 executing on the handheld devices. SW 118 enables an administrator, through interface with server 101 and access to data stored in repository 102, to create and hold accounts pertaining to neurocognitive and psychomotor performance testing and patient care, and to provide, store and access data pertinent to specific patients relating to baseline, post injury or recovery, and symptom data. In one embodiment server 101 may also execute an instance of SW 123, or a module(s) thereof to further facilitate administration of accounts and data gathering and interpretation in practicing the invention. In one embodiment SW 118 executing on computer 120 enables an administrator to remotely administer neurocognitive and psychomotor performance testing procedures in the field via the handheld devices, as will be described later in the specification in further detail. Computer 120 represents one or a plurality of computers executing one or a plurality of instances of SW 118.

The architecture described above with reference to FIG. 1 embodies a basic system configuration in which the present invention may be implemented in accordance with a preferred embodiment of the present invention. The system of the invention provides solutions to all of the problems in state of the art systems as described in the background section by providing a simple, low-cost, portable and flexible computerized human neurocognitive and psychomotor performance testing and evaluation tool for aiding administrators in the initial diagnosis of acute concussion while in or near the field location of an injury. The system provides many of the cognitive and physical performance test batteries not available in state of the art portable handheld diagnostic devices, and is capable of generating point-of-use reporting for comparing real time test result data with normative and/or past test result data stored locally or remotely for timely, accurate and appropriate diagnostic decision making, as well as providing for remote subject account administration and test module authoring, and inter-device data sharing as well as that between field and host devices and central mass data storage, Such interconnection allows the handheld devices to operate in conjunction with host desktop or laptop computers for test battery creation and configuration, complex data analysis and archival data storage.

Figure 2:
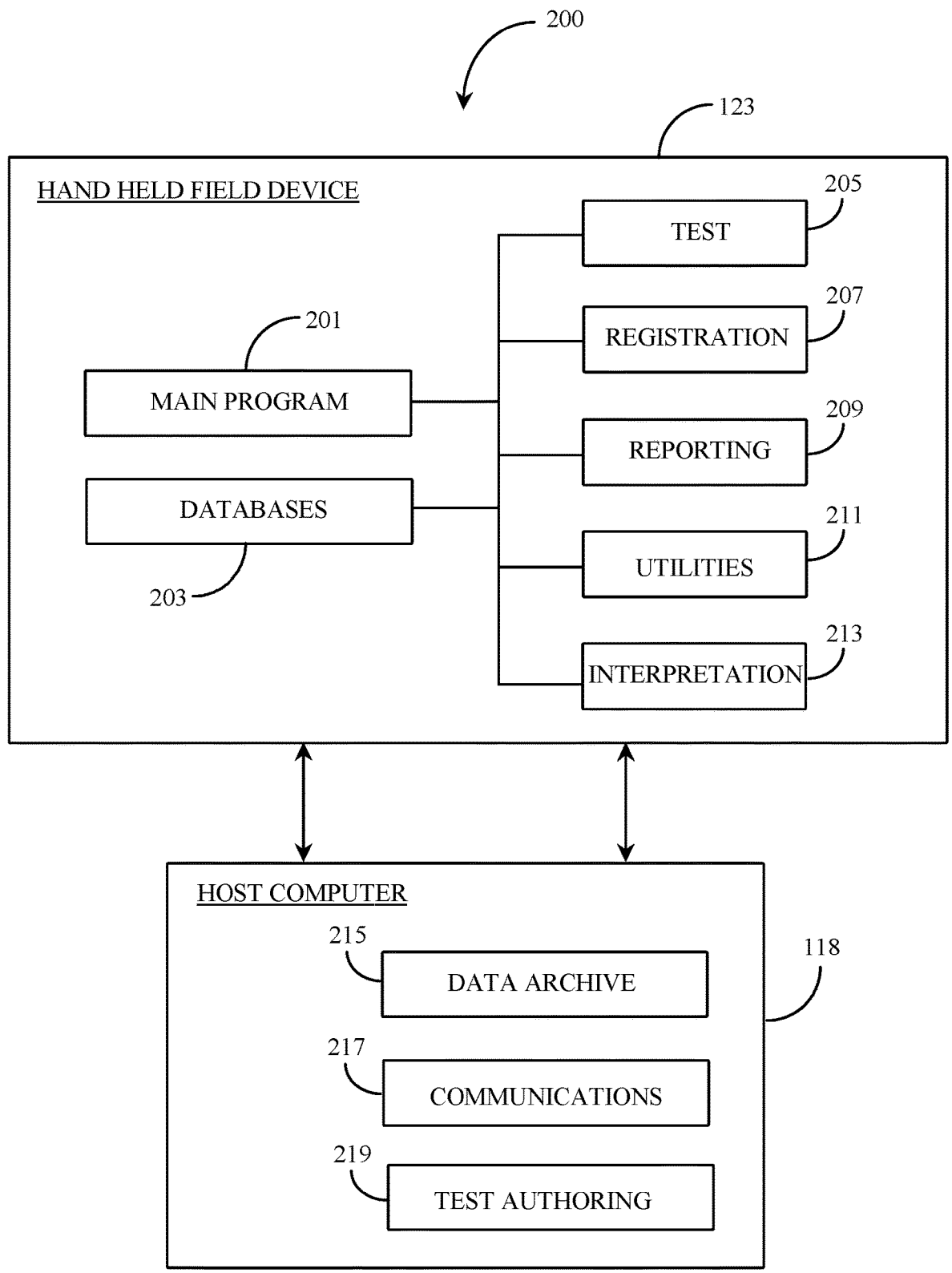
FIG. 2 is a block diagram representing functional units of the evaluation and testing system of FIG. 1.

FIG. 2 is a block diagram representing various functional units of the neurocognitive evaluation and testing system software (SW 123) executing on device(s) 109 and 110, as well as other data collection, archiving/processing, authoring and other administrative functions as executed by host software (SW 118) of computer(s) 120 as illustrated in FIG. 1 according to an embodiment of the invention. System 200 comprises various components executing on one or a plurality of handheld field computing devices as well as one or a plurality of host computers, which may be home or business-based computers interconnected over a wide area network such as the Internet. Components of the software system include a main program 201 and various integrated modules including those for testing, registration, reporting, utilities and interpretation.

Main program 201 of the exemplary embodiment of the neurocognitive assessment and evaluation system 200 controls all critical system functions including test administration, data collection, system security data encryption access to restricted system features and communication with a host computer using a variety of connection means including Internet and wireless, radio frequency, serial, USB, IR or dial-up modem. The main program further permits recording of notes before and after test administration and allows test responses from test subjects to be recorded for comparative analysis, and may include voice recognition capability.

System 200 runs testing modules 205 in test batteries designed to meet specific operational and clinical goals, utilizing test modules derived from standardized metrics which evaluate fatigue and energy levels, ability to sustain concentration and attention, spatial processing, working memory and other tests which evaluate overall cognitive efficiency. For the first time in the art of endeavor system 200 also runs non-standardized test modules in batteries designed for evaluating physical balance and performance measures including eye movement tracking; all executable and interpretable from a small, portable handheld computing device operational in the field at or near the location of a suspected or witnessed acute concussion brain injury.

A subject registration module 207 may permit secure use of the same neurocognitive and psychomotor performance assessment and evaluation system by multiple test subjects through the use of a Personal Identification (PIN) System. For example, a system that is loaded onto a portable handheld computing device such as device 109/110 (FIG. 1) can be available to an administrator for testing of any member of a sports team to evaluate and initially diagnose an acute concussion due to a suspected or witnessed head trauma injury in the field. The administrator may utilize a PIN specific to an individual who has previously provided baseline information to the system, or who has been previously tested and the test results have been archived in a data repository, such as repository 102 (FIG. 1), or in resident memory of the handheld computing device or host computer. In this case the test results associated with a particular test subject are accessed each time the subject's specific PIN is entered at login. Further, the PIN system prevents accidental or deliberate manipulations of test results associated with a particular subject. Data for the subject may then be collected over time to evaluate the test results of each subject, as well as the entire sports team.

The registration modules 207 allow secure testing on a single system 200, and interpretation modules 213 and reporting modules 209 are customized for specific test batteries and applications. Interpretation modules 213 use a variety of predefined standardized criteria for evaluating test performance including demographic, age/sex and other specific norms, including the subject's own historical test performance result data. Status reports are generated from the reporting modules 209, and may provide immediate feedback when a test battery is completed. System 200 also includes a utility module 211 executable on the handheld device that facilitates data transfer from the handheld device to a host computer such as a desktop or laptop computer, and test battery installation from the host computer to the handheld computer using a variety of connection means. Utilities module 211 allows the handheld computer to operate in conjunction with a host desktop or laptop computer for not only test battery creation and configuration, but also for complex test result and other data interpretation and analysis and for archival data storage.

System 200 as exemplarily illustrated in FIG. 2 has the main program 201, databases 203, and modules for test 205, registration 207, reporting 209, utilities 211 and interpretation 213 executing on the handheld field device, said program components which are represented by SW 123 hosted by handheld computing device 109/110 (see FIG. 1), and modules for data archive 215, communications 217 and test authoring 219 executing on the host computer, which are represented as SW 118 executing on computer 120 (see FIG. 1). However, in other embodiments of the invention, some modules and components of the software system may be distributed between the field and host devices differently from that illustrated in FIG. 2 without departing from the overall scope and spirit of the invention. The specific modules executing on specific devices should in no way limit applicant's invention.

Figure 3:
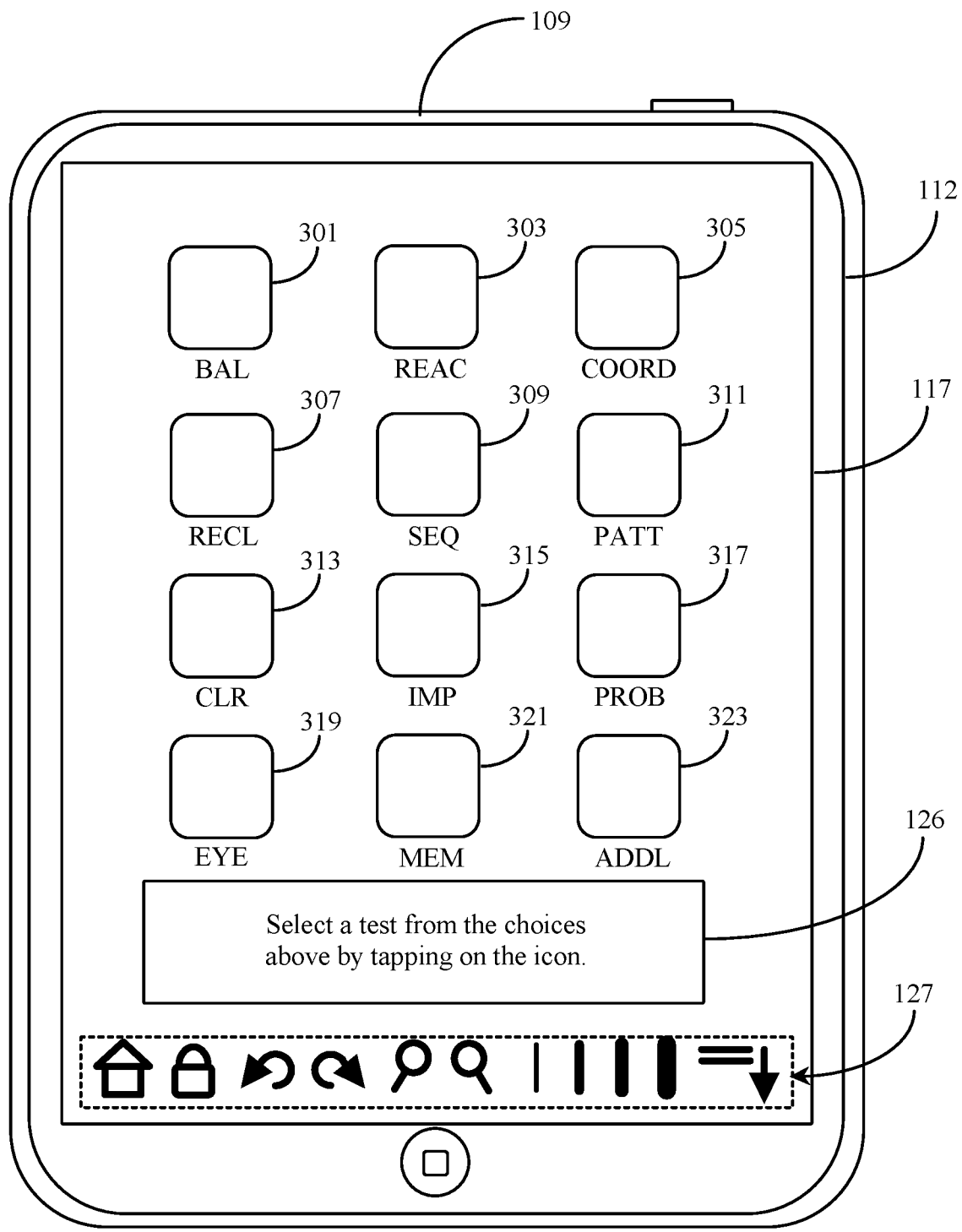
FIG. 3 is an illustration of a handheld device which may be used to implement the evaluation and testing system, displaying a battery of tests according to a preferred embodiment of the present invention.

FIG. 3 illustrates a handheld device 109 which may be used to implement a neurocognitive and psychomotor performance evaluation and testing system according to a preferred embodiment of the present invention. Device 109 in the example illustrated is an iPad™ tablet computing device, which provides a host of features and computing capability which maximizes the utility of applicant's invention, in a portable handheld and comparatively inexpensive portable device. However it is important to note that not all of the features typically found in modern tablet computers are required to practice the invention, and other like devices may also be utilized without departing from the spirit of the invention.

Device 109 comprises a screen area 112 which utilizes touch screen technology which may be resistive type which can respond to any kind of pressure applied to the screen and allow a high level of precision, or the touch screen may be of the capacitive type which is somewhat less accurate but more responsive than resistive screens. Ease of use fingertip input without the use of a stylus is preferable, and multi-touch capability which can recognize multiple simultaneous finger touches may also be incorporated. Screen area 112 comprises a view area 117 which displays various icons for finger touch selection, and located below the icon display area is a dialog box 126 which provides textual information and instructions, etc., pertaining icon selections made by the user. A toolbox area 127 is located below dialog box 126, and comprises various finger-selectable icons representing tools, utility and navigation buttons. Illustrated from left to right in the toolbox area 127 are: "home" for navigating to a main menu, "padlock" for viewing and editing secure data pertaining to specific registered test subjects or administrators, "undo and redo" of previous selections, "zoom" for magnifying specific portions of display, "display weight" for display boldness level, and a "pull down" menu or "scroll" list menu button for expanding on upper level category displays or for scrolling through a list of registered test subjects, for example. View area 117 changes display according to selections made by the user.

In the example illustrated in FIG. 3, view area 117 displays in the main area above the dialog box a plurality of icons representing a battery of test modules. Device 109 executes an instance of applicant's neurocognitive and psychomotor performance testing program (SW 123, FIG. 1). It can be assumed for example that a test administrator has powered on device 109 for the purpose of administering a neurocognitive and/or psychomotor performance test to an injured person suspected of having a possible acute concussion, and is thus presented with a login main screen (not shown) in which a PIN is entered to identify the administrator who has previously used the system and holds an account as an authorized qualified test administrator. Once logged in and authorized by the system the administrator may select the test subject from a list of names of past test subjects, and if so, the administrator may enter an additional PIN associated with that subject whose historical test data may be stored in a data repository, and thus becomes available to the administrator. Or if necessary, the administrator may create a new record for a test subject with no system history or stored data.

Regardless, in the example illustrated in FIG. 3 a plurality of icons representing test modules is displayed. The table below lists each test module and briefly describes each:

TABLE 1

301 BAL Physical: balance ability
303 REAC Physical: reaction time
305 COORD Physical: coordination
307 RECL Cognitive: recollection
309 SEQ Cognitive: next in sequence identification
311 PATT Cognitive: pattern recognition
313 CLR Cognitive: color recognition
315 IMP Physical: impulse control
317 PROB Cognitive: problem solving
319 EYE Physical: eye movement tracking
321 MEM Cognitive: measures short and long term memory
323 ADDL Additional modules (pg. 2, 3 . . . )

By tapping a test icon as illustrated in view area 117 of device 109 in FIG. 3, the administrator is presented with a screen display of the test associated with that icon. The following description of FIGS. 4-14 provide an understanding of several of the tests available and provided by the system as listed in Table 1 above and illustrated by the exemplary screen shots representative of each test. The invention should by no means be limited to those illustrated and described in the foregoing description in the specification. Many other such tests may be implemented by the system without departing from the scope and spirit of the invention.

Figure 4:
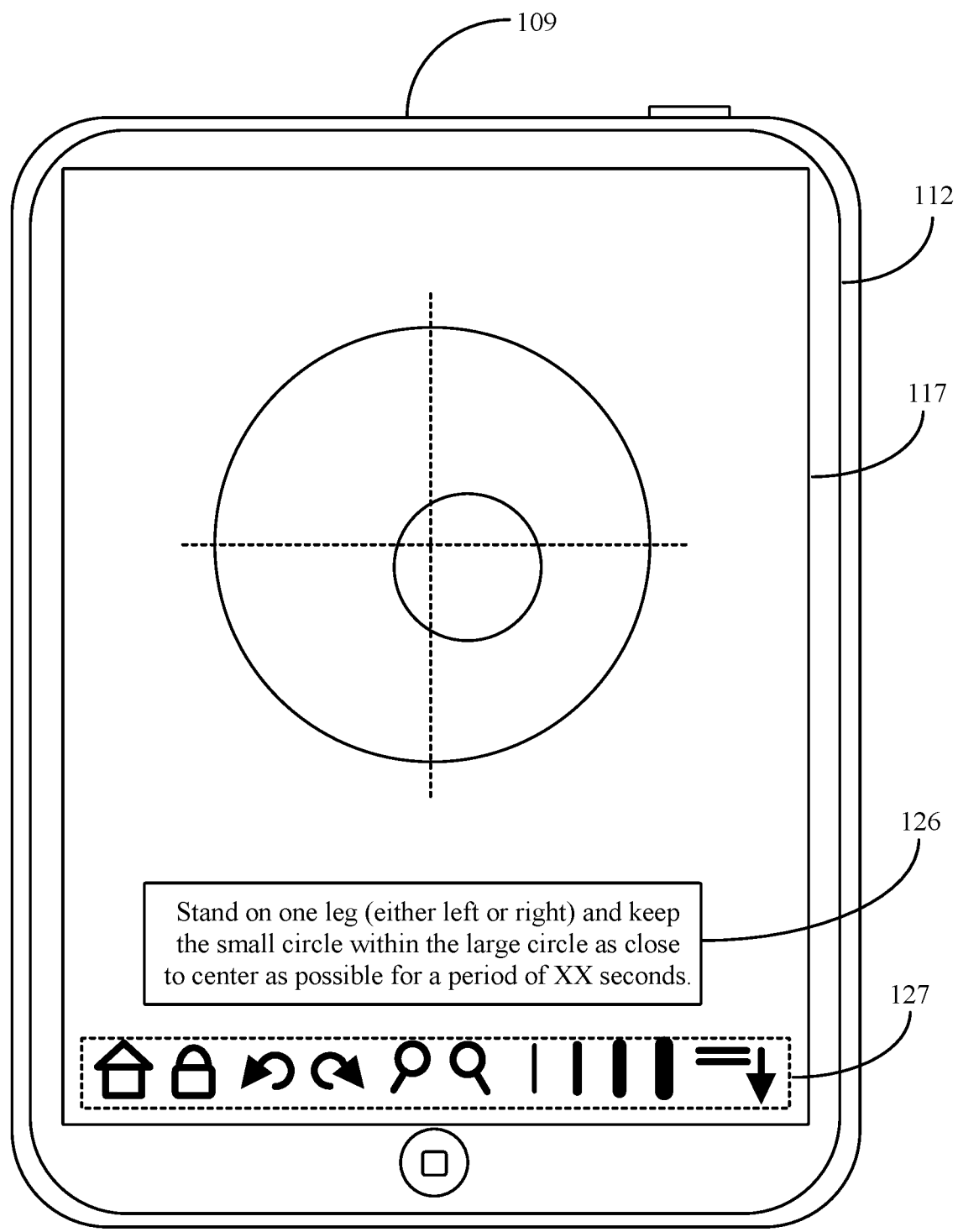
FIG. 4 is an illustration of the handheld device of FIG. 2, displaying a balance test component of the testing program according to an embodiment of the invention.

FIG. 4 illustrates the handheld device 109 of FIG. 2, displaying an example of a balance test which is activated by the user tapping the BAL 301 icon (FIG. 3). As previously mentioned with reference to FIG. 1, handheld device 109/110 features an accelerometer function which detects the physical movement of the device itself, and can also be used to detect the orientation of the device relative to the center of the earth. In this example a fixed large circle is displayed in view area 117 of screen area 112, and a floating smaller circle is also displayed. Dialog box 126 displays test instructions for the person to stand on one leg and keep the small circle within the boundaries of the larger circle for a period of time. The accelerometer function of the device detects orientation of the device itself relative to the center of the earth, and moves the small circle relative to the fixed larger circle depending on the angle of the device relative to vertical, as held by the person taking the test. The test is timed, and started and stopped by tapping the touch screen 112 for example, or by tapping an icon (not shown) in toolbox area 127 to repeat the test. The test is repeated for X number of times, and the test results are a percentage of time the tested person is able to maintain the small circle within the larger one.

Figure 5:
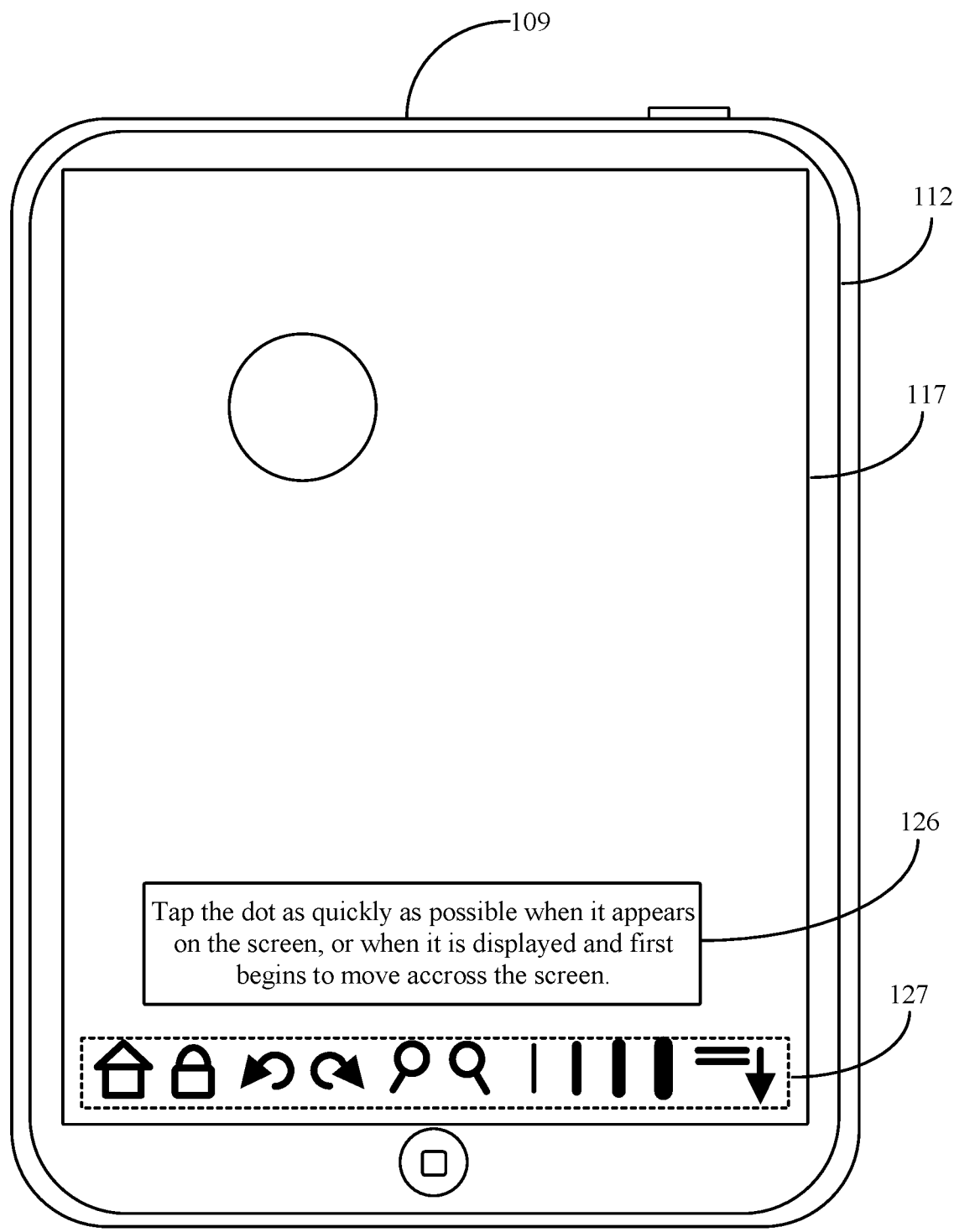
FIG. 5 is an illustration of the handheld device of FIG. 2, displaying a reaction time test component of the testing program according to an embodiment of the invention.

FIG. 5 illustrates the handheld device 109 of FIG. 2, displaying an example of a reaction time test which is activated by the user tapping the REAC 303 icon (FIG. 3).

In this example a fixed dot is intermediately displayed in view area 117 of screen area 112, and the dot may appear and then disappear quickly, or mat appear stationary and then begin to move across view area 117 in different directions. Dialog box 126 displays test instructions for the person to tap the dot as quickly as possible when it first appears on the screen, or when it is already displayed as stationary and first begins to move across the screen. The time between when the dot first appears and when the person taps it is timed and measured, as is the time between when the dot first begins moving across the screen and it is tapped. The test can be started and stopped by tapping the touch screen 112 for example, or by tapping an icon (not shown) in toolbox area 127 to repeat the test. The test is repeated for a selected number of times, and the test results are an average of all the reaction times measured between appearance of the dot and dot tap, and moving of the dot and dot tap.

Figure 6:
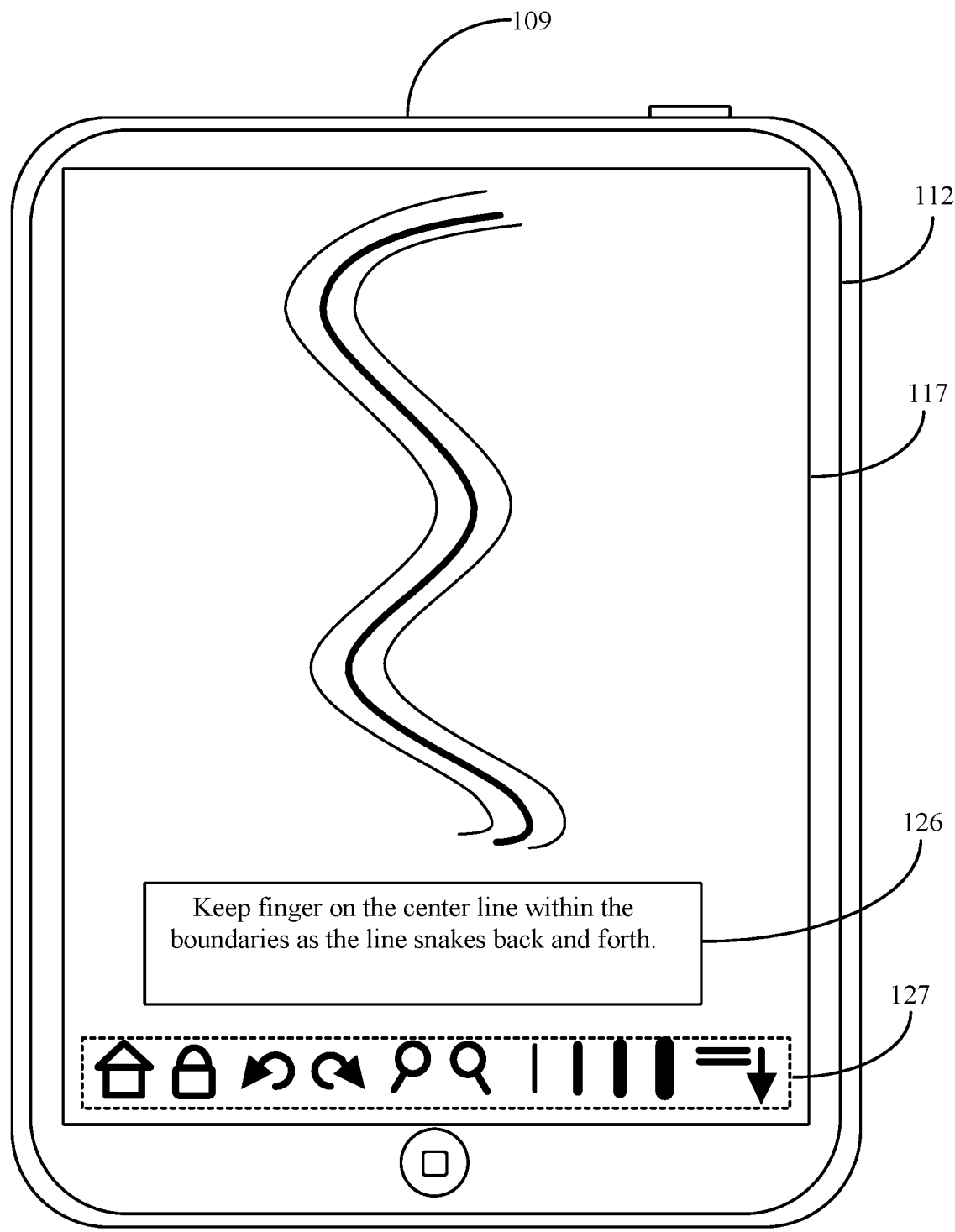
FIG. 6 is an illustration of the handheld device of FIG. 2, displaying a coordination test component of the testing program according to an embodiment of the invention.

FIG. 6 illustrates the handheld device 109 of FIG. 2, displaying an example of a physical coordination test which is activated by the user tapping the COORD 305 icon (FIG. 3). In this example an S-curved line with boundary is displayed in view area 117 and the line continually snakes back and forth across the viewing area, increasing in movement speed as it continues. Dialog box 126 displays test instructions for the person to keep a finger placed on the center line within the boundaries as it snakes back and forth. In another example of such a test the user can be instructed to keep the finger placed on an iconic representation of a car as if the car was travelling down the center line of a windy road. The instances of the user's finger venturing outside the boundaries of the center line as it snakes back and forth and continually increases in speed are recorded by the software, and the test discontinues if for example the user's finger ventures outside the boundaries for three times total, as an example. The test can be stopped or restarted by tapping the touch screen 112 for example, or by tapping an icon (not shown) in toolbox area 127. The test results are the total length of time the user was able to continue the test(s) successfully.

Figure 7:
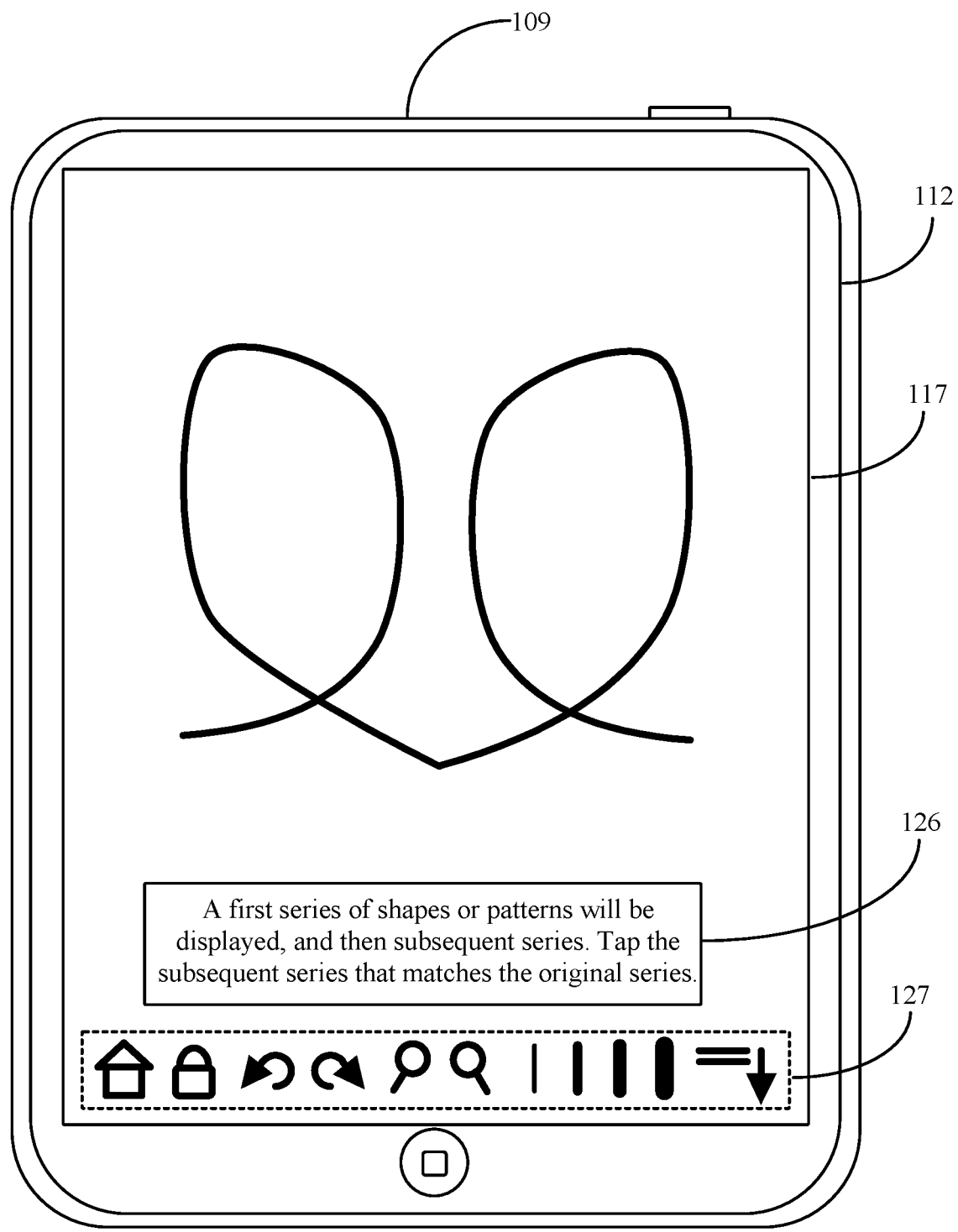
FIG. 7 is an illustration of the handheld device of FIG. 2, displaying a visual memory test component of the testing program according to an embodiment of the invention.

FIG. 7 illustrates the handheld device 109 of FIG. 2, displaying an example of a pattern recognition test which is activated by the user tapping the PATT 311 icon (FIG. 3). In this example of a short-term memory test, a series of shapes or patterns are alternately displayed in view area 117. Several series of similar shapes and patterns are subsequently displayed, and the user is asked in dialog box 126 to tap the series that matches the original one. This process is repeated for X number of times, and the test results are the total number of correct matches. The test can be stopped or restarted by tapping the touch screen 112 for example, or by tapping an icon (not shown) in toolbox area 127. The test results are the total length of time the user was able to continue the test(s) successfully.

Figure 8:
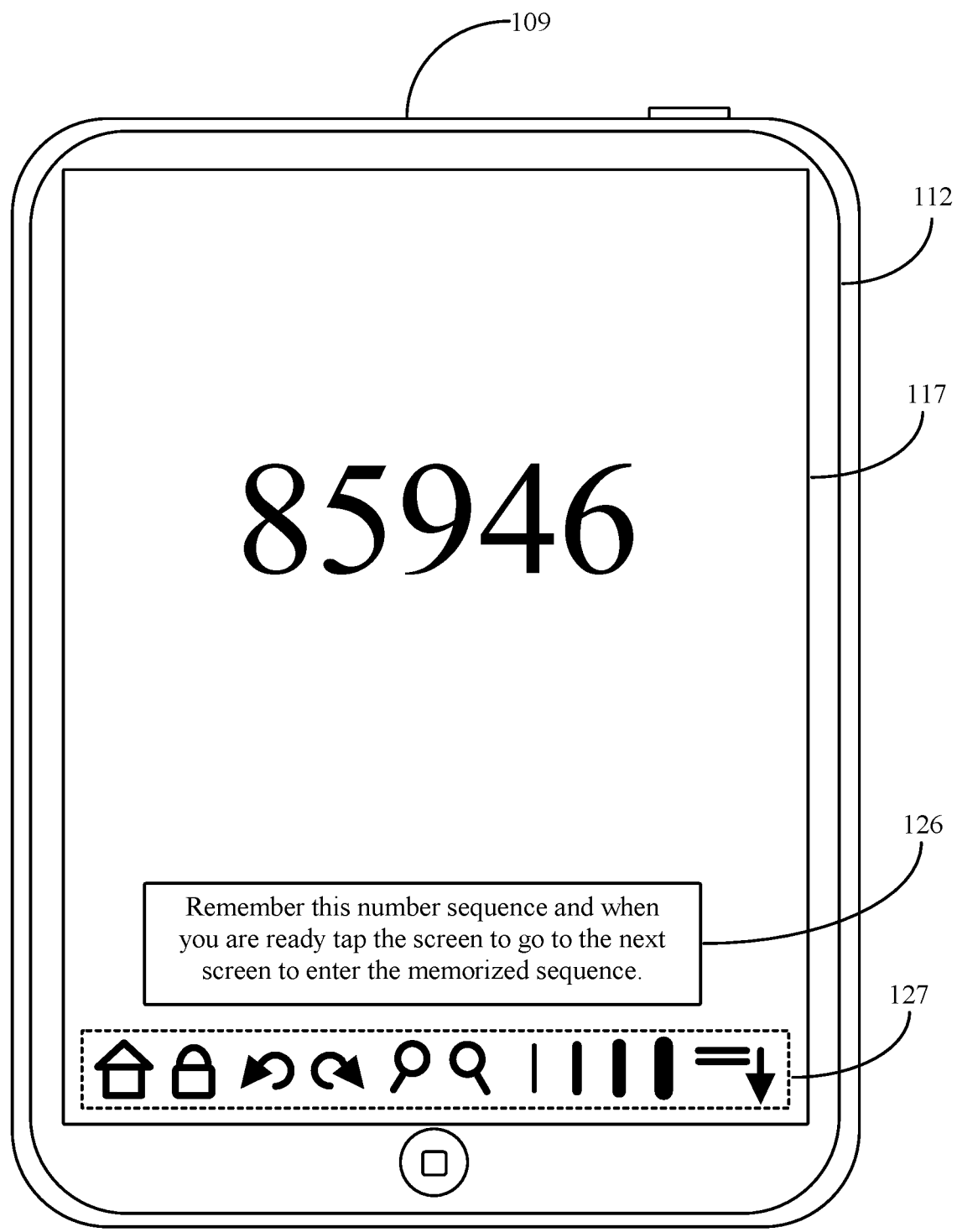
FIG. 8 is an illustration of the handheld device of FIG. 2, displaying a short and long term sequence memory test component of the testing program according to an embodiment of the invention.
Figure 9:
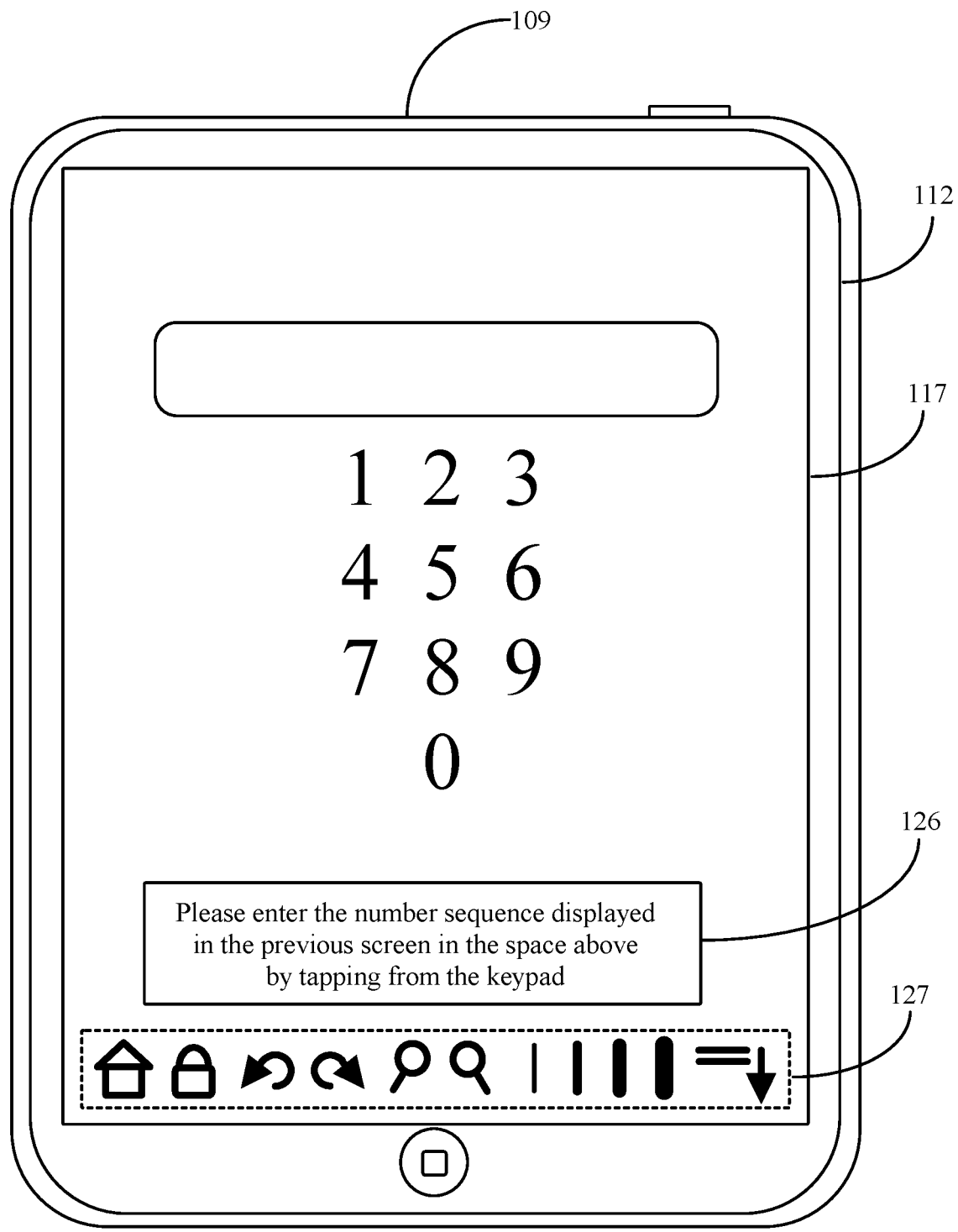
FIG. 9 is an illustration of the handheld device of FIG. 2, displaying a graphical interface to enter the sequence displayed in FIG. 8 according to an embodiment of the invention.

FIG. 8 illustrates the handheld device 109 of FIG. 2, displaying an example of a memory test, which is activated by the user tapping the MEM 321 icon (FIG. 3). In this example of a short and long-term memory test, in a first screen a sequence of numbers is displayed and the user is instructed in dialog box 126 to remember the sequence and tap the screen to go to a next (second) screen where the user can manually enter the sequence in a box provided by tapping the numbers displayed in view area 117 as a numeric pad. FIG. 9 illustrates the second screen of the memory test for inputting the memorized sequence. In another example (short-term memory test) several words can be initially displayed for memorization, and the words may then be immediately entered in the second screen (FIG. 9) by tapping letters displayed in a text keypad, or identified from a list of words displayed on the view screen by immediately tapping on the matching words. As an example of long-term memory test, at the very end of the test the user can be instructed to identify all of the previous words (or number sequences) displayed throughout the test from a list, by tapping the words or sequences displayed in the list. The test results are a determination of how many of the words or sequences are correctly identified. The test can be stopped or restarted by tapping the touch screen 112 for example, or by tapping an icon (not shown) in toolbox area 127.

Figure 10:
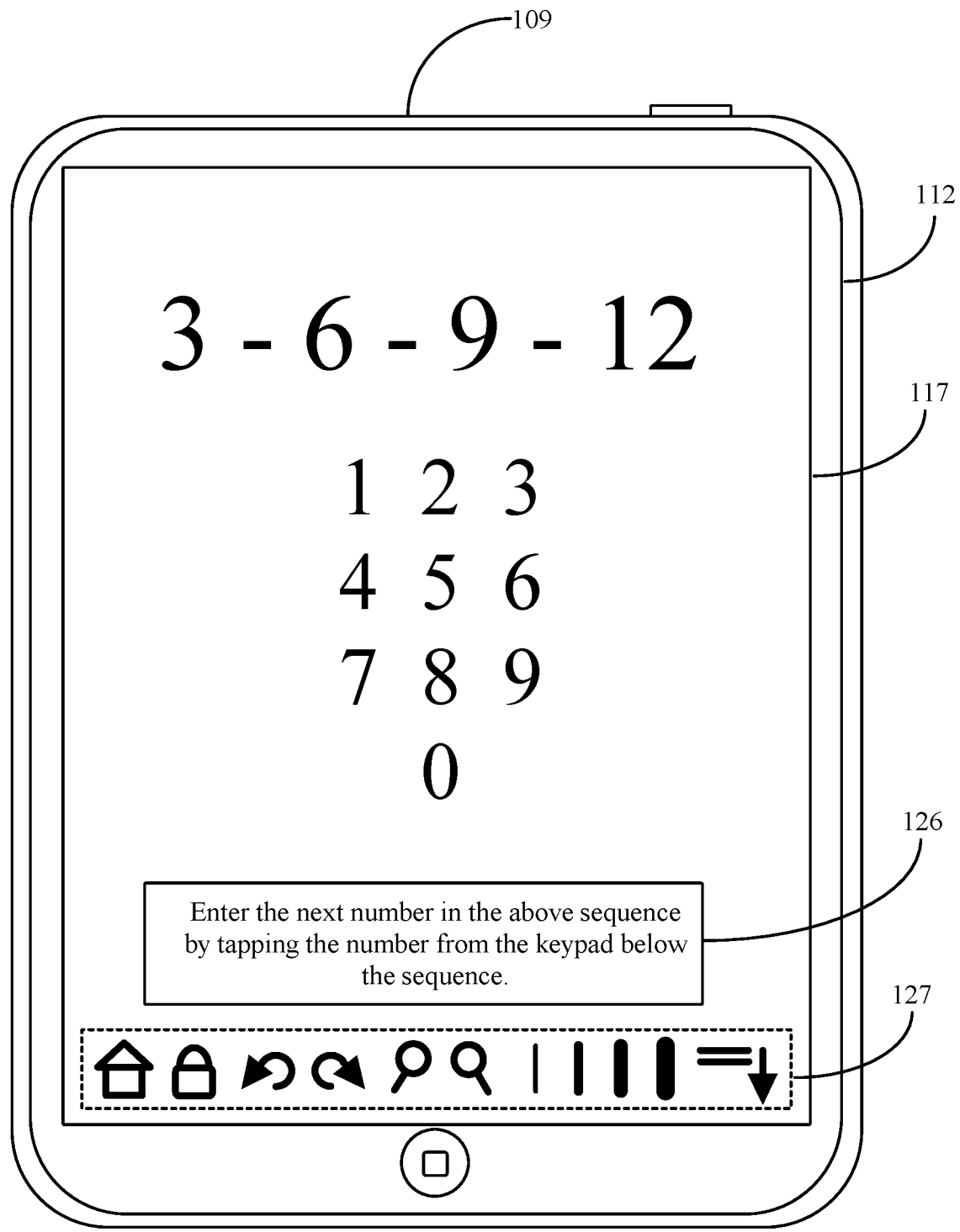
FIG. 10 is an illustration of the handheld device of FIG. 2, displaying a problem solving test component of the testing program according to an embodiment of the invention.

FIG. 10 illustrates the handheld device 109 of FIG. 2, displaying an example of a problem-solving test which is activated by the user tapping the PROB 317 icon (FIG. 3). In this example various sequential patterns of numbers displayed in view area 117, for example 3, 6, 9, 12. The user is asked in dialog box 126 to enter the next number in the sequence by tapping the number out using the numeric keypad below the sequence. This process repeats for X number of times using different sequential or other patterns. The sequence can in another example comprise of alpha characters or words. Test results are the total number of correct answers, and also the elapsed time it took the user to complete the test. The test can be stopped or restarted by tapping the touch screen 112 for example, or by tapping an icon (not shown) in toolbox area 127.

Figure 11:
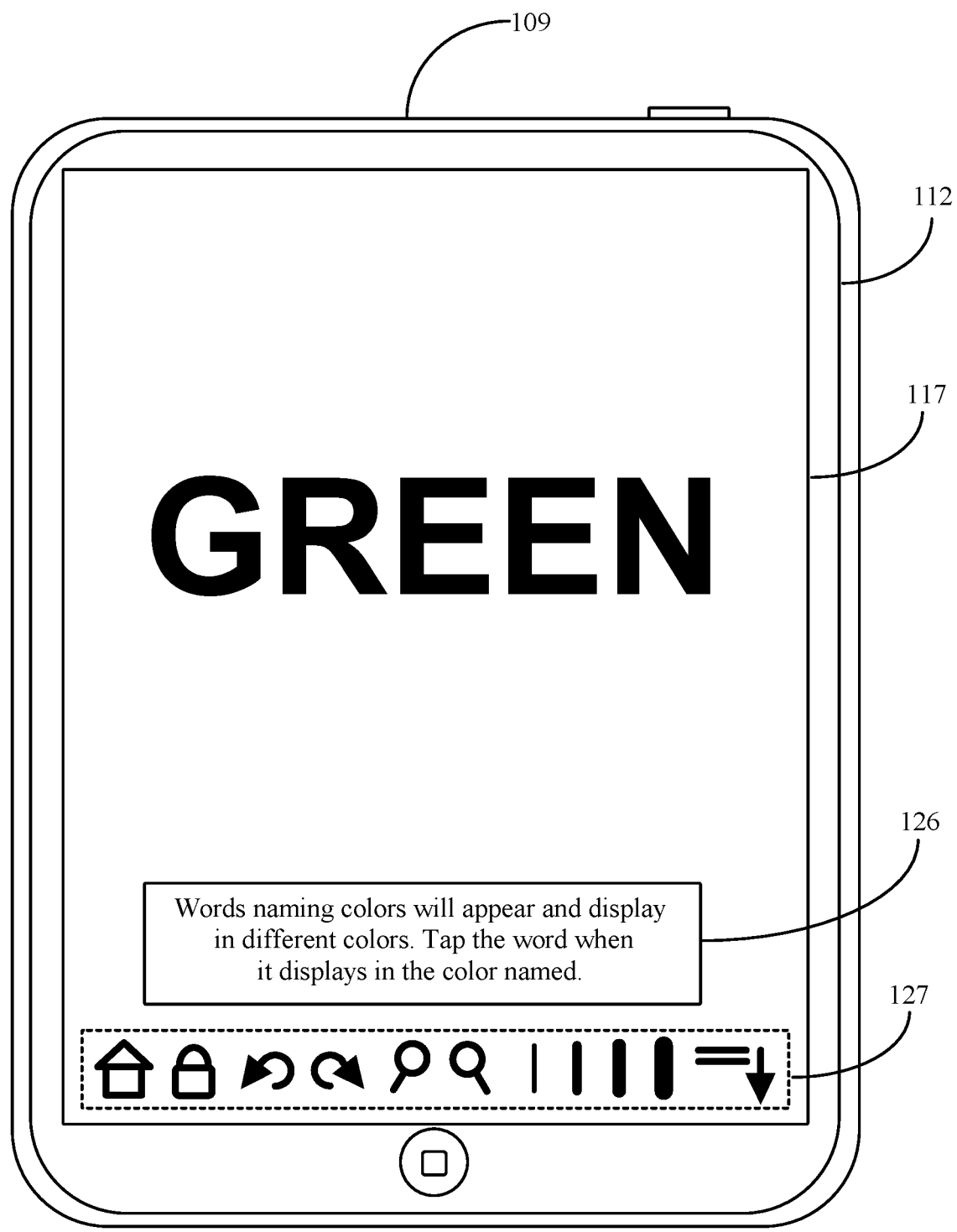
FIG. 11 is an illustration of the handheld device of FIG. 2, displaying a color recognition test component of the testing program according to an embodiment of the invention.

FIG. 11 illustrates the handheld device 109 of FIG. 2, displaying an example of a color recognition test which is activated by the user tapping the CLR 313 icon (FIG. 3). In this example in view area 117 a word is displayed in a particular color. The displayed color of the word may not necessarily match the color it names. For example the word "RED" may be displayed in purple letters, and so on. The process repeats by other words appearing in different colors. The user is instructed in dialog box 126 to tap on the word when it is displayed in the color it names. This process repeats X number of times. The test results are the total number of correct matches. The test can be stopped or restarted by tapping the touch screen 112 for example, or by tapping an icon (not shown) in toolbox area 127.

Figure 12:
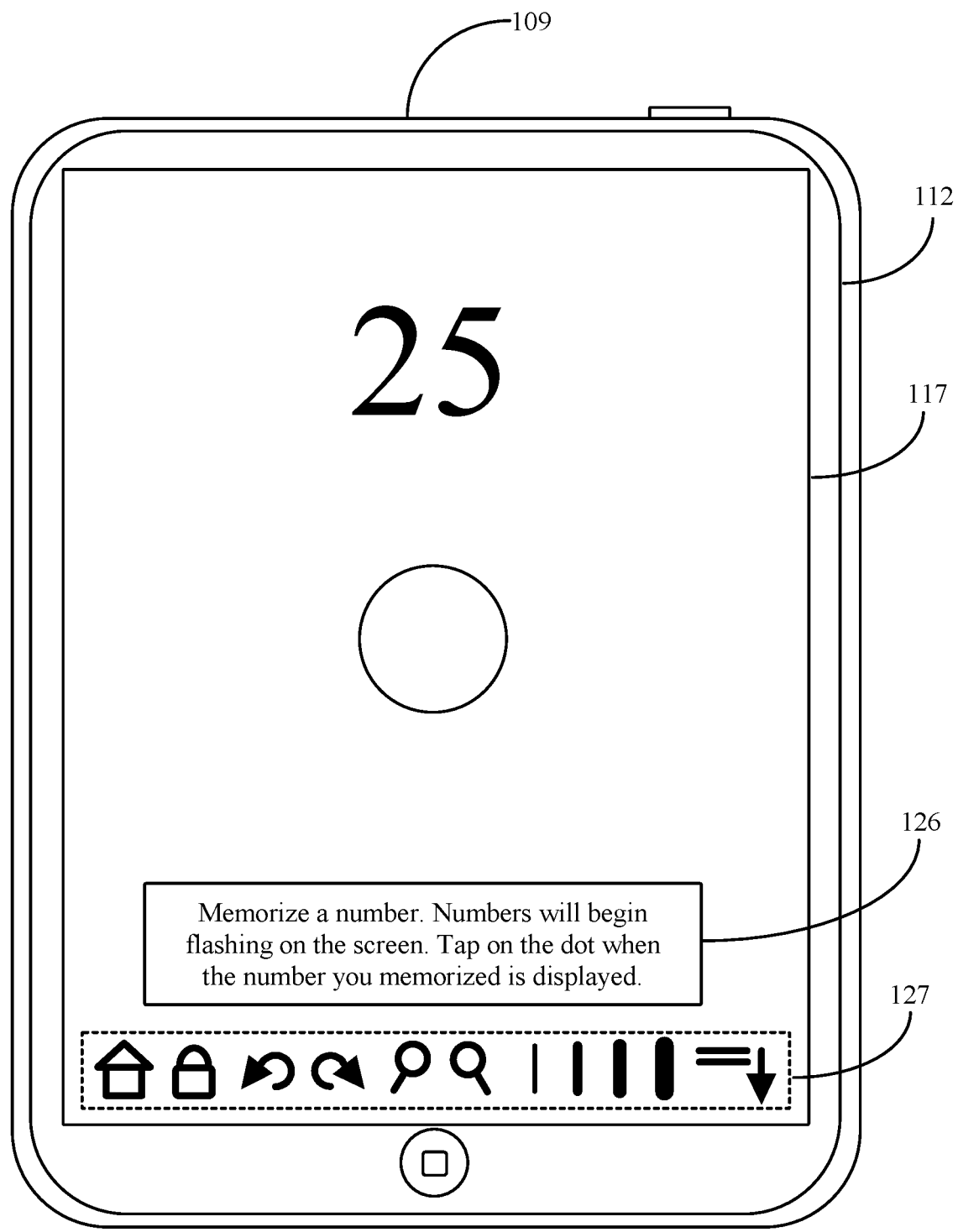
FIG. 12 is an illustration of the handheld device of FIG. 2, displaying an impulse control test component of the testing program according to an embodiment of the invention.

FIG. 12 illustrates the handheld device 109 of FIG. 2, displaying an example of an impulse control test which is activated by the user tapping the IMP 315 icon (FIG. 3). In this example the user is instructed in dialog box 126 to memorize a number. The user may then tap screen area 112 for example to begin a series of numbers flashing in view area 117. The user is instructed to tap on a dot displayed in the view area when the number they memorized is flashed on the screen. During the test the user may be shown flashing numbers leading up to, or down to the memorized number. For instance, if the number memorized is 25, the flashing sequence may be 21, then 22, 23, 24 . . . and the memorized number (25) may follow as expected, or a random number other than 25 may appear following 24. This may also be a reverse sequence such as 29, 28, 27, 26 . . . , and either the expected memorized number (25) will appear, or a random number other than 25 may follow 26. The test results are the total number of correct responses when the user was expecting the memorized number, it flashes and the dot is immediately tapped. This process repeats X number of times. The test can be stopped or restarted by tapping touch screen 112 for example, or by tapping an icon (not shown) in toolbox area 127.

Figure 13:
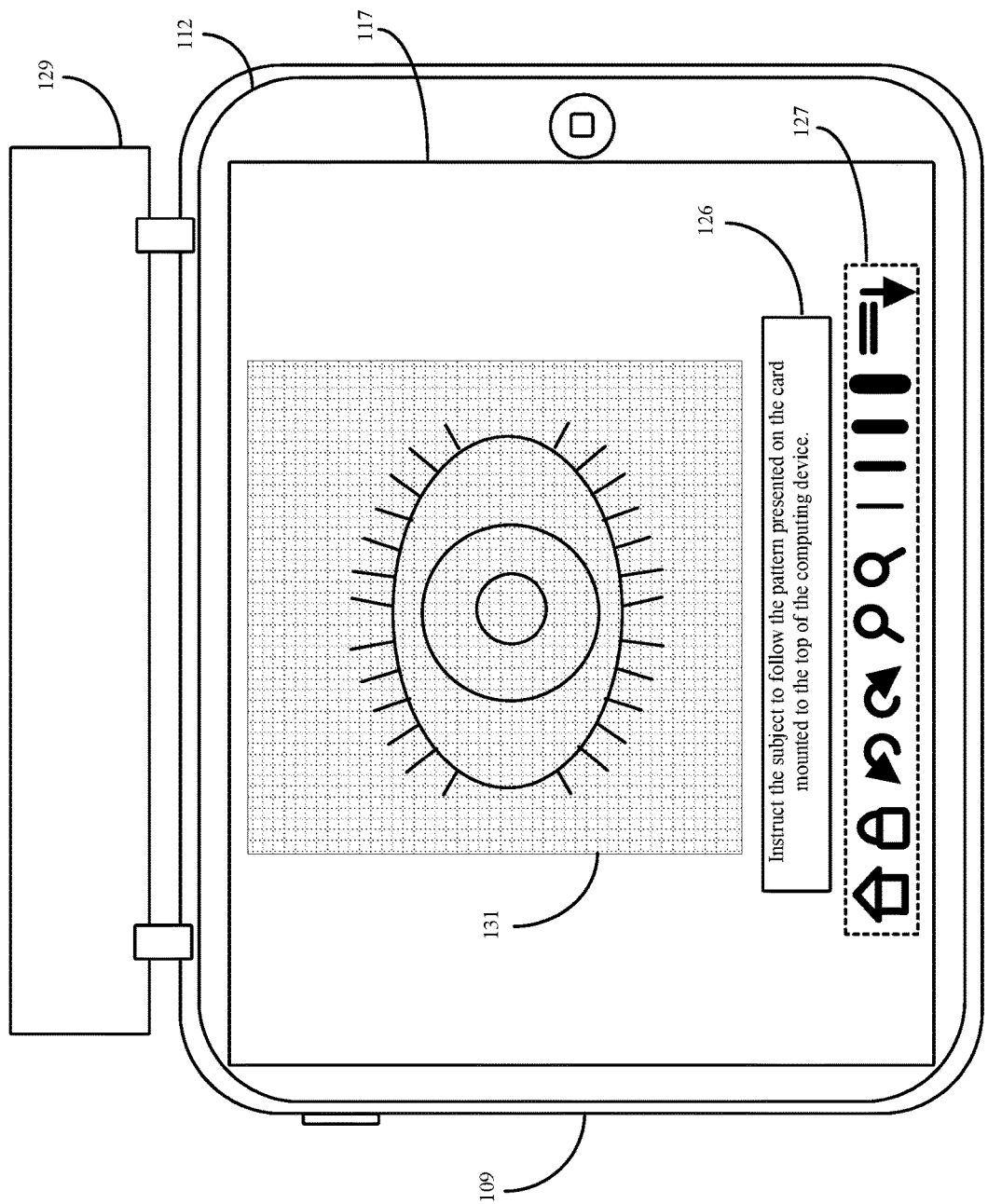
FIG. 13 is an illustration of the handheld device of FIG. 2, displaying an eye movement tracking test component of the testing program, and tracking guide attachment according to an embodiment of the invention.

FIG. 13 is an illustration of the handheld device of FIG. 2, displaying an eye movement tracking test component of the testing program, and tracking guide attachment according to an embodiment of the invention. The eye tracking test is activated by the user tapping the EYE 319 icon (FIG. 3). In this example the test procedure utilizes the camera function of device 109 to capture and record a user's eye movement. In a preferred embodiment as previously described with reference to FIGS. 1 and 2, device 109 is an iPad™ which incorporates a built in camera including video capture capability. As is well known the camera's eye is located on the surface of the device opposite the display screen. The eye tracking test component according to a preferred embodiment includes SW functionality having the capability of capturing a subject's eye movement utilizing the video capture function and tracking the eye movement using a grid system as represented by grid 131. View area 117 displays an image of the subject's eye with grid 131 superimposed.

An eye tracking guide 129 is illustrated in this embodiment, fixedly attached to the top of device 109. Although not seen in this view, guide 129 displays a pattern on the surface facing away from the screen area of the device, and therefore facing and visible to a test subject. The pattern displayed on the guide is known to the SW of the test program of the testing SW executing on device 109. The pattern is known by the software in relation to grid 131, and the SW also knows the relative proximity between the pattern display guide 129 and that of the camera eye of device 109.

Upon commencement of the test which is activated by the administrator tapping the EYE 319 icon (FIG. 3) the video capture and record capability of device 109 is started, and the test administrator is instructed in dialog box 126 to advise the test subject to follow the pattern of the display guide 129 while the administrator focuses the camera on the subjects eye. The SW is enabled to therefore track movement of the test subject's eye as it follows the displayed test pattern, and records the eye movement in relation to grid 131. Deviations in the actual movement of the subject's eye from the displayed test pattern of guide 129 are recognized and recorded, thereby providing data for evaluation of impaired eye movement which may be indicative of symptoms of acute concussion or other MTBI.

Figure 14:
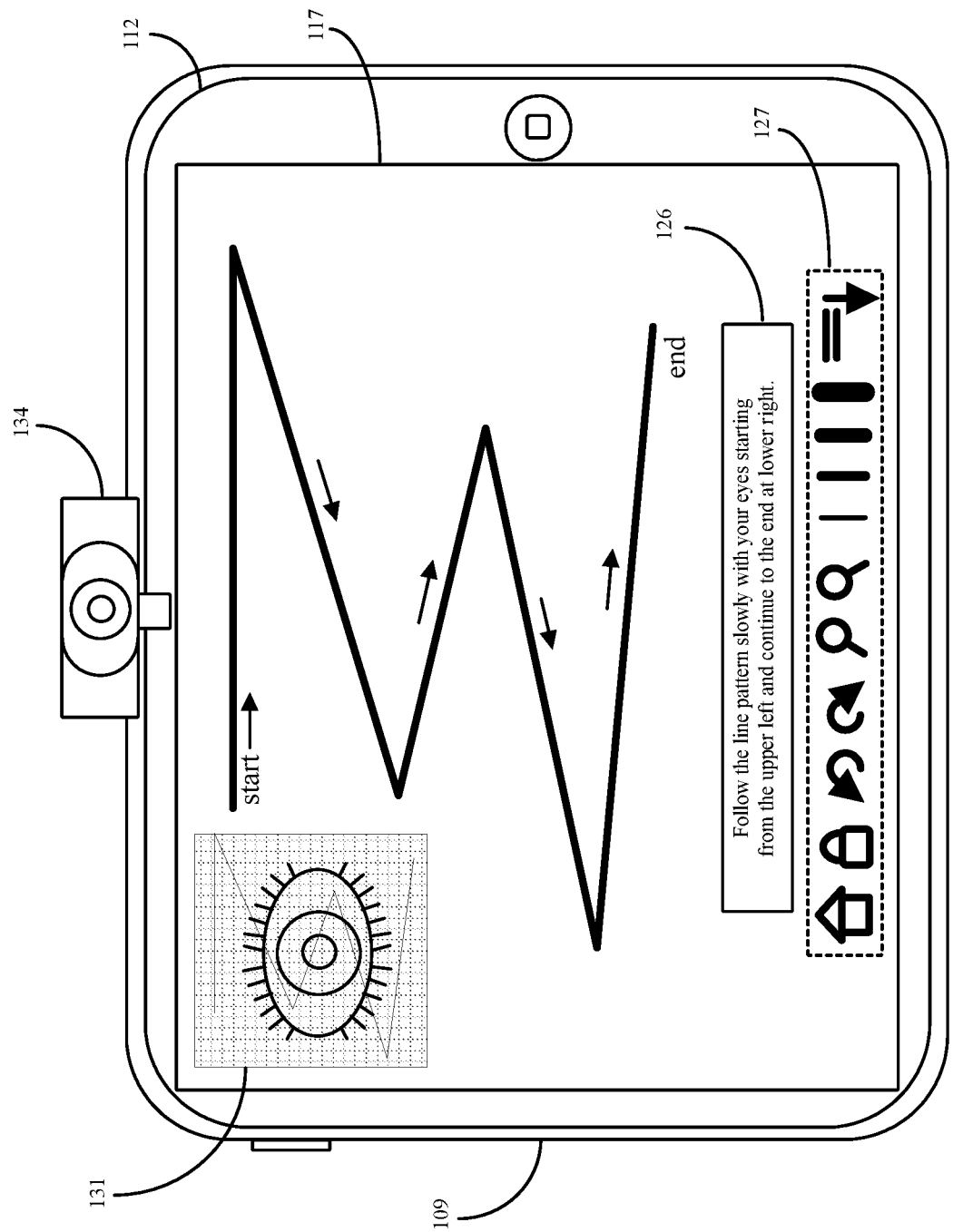
FIG. 14 is an illustration of the handheld device of FIG. 2, displaying an eye movement tracking test component of the testing program, and an auxiliary video capture attachment according to an embodiment of the invention.

FIG. 14 is an illustration of the handheld device of FIG. 2, displaying an eye movement tracking test component of the testing program, and an auxiliary video capture attachment according to another embodiment of the invention. The example illustrated is a test procedure similar to that illustrated and described above with reference to FIG. 13, with the exception that a test subject is enabled by the SW capability to self-administer the test without the need for a test administrator. This is enabled because the test subject is able to view the test pattern to follow with the eyes as it is displayed in view area 117. Further enablement is possible in this embodiment as device 109 has a camera attachment 134 which faces the viewer on the touch screen-side of the device, and which is fixedly attached to the top of device 109.

As in the embodiment of FIG. 13, the eye tracking test in this embodiment is activated by the user tapping the EYE 319 icon (FIG. 3), and the test procedure utilizes the video capture function of rearward-facing camera attachment 134 to capture and record the user's own eye movement. The SW functionality is capable of capturing the eye movement utilizing the video capture function and tracking the eye movement using a grid system as in the embodiment of FIG. 13. This embodiment differentiates from that of FIG. 13 in that the line pattern to follow with the eyes is displayed in view area 117 of the device touch screen. View area 117 also displays an image of the subject's eye with grid 131 as well as the line pattern superimposed, in a small area in the upper left corner of view area 117. The eye-follow pattern displayed in area 117 is known to the SW of the test program of the testing SW executing on device 109. The pattern is known by the software in relation to grid 131, and the SW also knows the relative proximity between the pattern displayed and that of the eye of camera attachment 134.

Upon commencement of the test activated by the invoking the EYE 319 icon (FIG. 3) the video capture and record capability of device 109 is started, and with possibly a screen tap the self-tester is instructed in dialog box 126 to follow the line pattern slowly with eyes from upper left to lower right of the pattern. The SW is enabled to therefore track movement of the self-test subject's eye as it follows the displayed test pattern, and records the eye movement in relation to grid 131. Deviations in the actual movement of the subject's eye from the displayed test pattern of guide 129 are recognized and recorded, thereby providing data for evaluation of impaired eye movement which may be indicative of symptoms of acute concussion or other MTBI.

Applicant's invention for the first time in the art of endeavor provides a simple, low-cost, portable and flexible computerized human neurocognitive performance testing and evaluation tool which aids medical professionals or other qualified administrators in quickly and determinately diagnosing acute concussions while in or near the field location of an injury to an individual suspected of sustaining a concussion or other MTBI, either due to a witnessed injury or an individual's display of possible acute concussion symptoms. The system provides all of the cognitive and physical performance test batteries, including those for coordination, balance and eye movement tracking to enable a person of ordinary skill in the art to more conclusively make a decision, while near or at the injury field location, as to whether or not an acute concussion exists, and generate point-of-use reporting which could provide immediate comparisons with normative data and/or to the injured person's past test performance so that timely, accurate and appropriate actions can be taken based on the test results.

The system could also be used in fields other than testing for acute concussion in field sports environments. For example, particularly due to the capability of testing for physical coordination and balance, a more particularly due to the eye movement tracking capability of the system, the invention could be advantageously used in field sobriety neurocognitive and psychomotor testing for the detection of neurocognitive/physical impairment in individuals suspected of being under the influence of mind, body and mood altering substances such as alcohol, illegal drugs and prescription or other medications. Other test batteries in various embodiments of the invention could be incorporated into the SW or may be created and installed, if desired, utilizing such as host computer 120 or another handheld computing device 109/110 (FIG. 1).

The system is simple and low-cost, provides software applications that are downloadable and installable on widely available low-cost handheld computing platform tablet devices such as Apple, Inc.'s iPad™ or Samsung's Galaxy Tab™, or Smartphone devices such as the iPhone™ or Nexus™ device, or other such devices in alternative embodiments of the invention. A plurality of the devices could be interconnected over a wide area network such as the Internet to enable inter-device data sharing as well as that between field and host devices and central mass data storage. If an acute concussion is determinate, subsequent retesting while still in the field can be performed to determine if the injured party had returned to either pre-injury performance or predefined age/sex specific norms, whereby the injured party could return safely to activity.

The invention has been described above with reference to exemplary embodiments, and therefore it should be understood by those with ordinary skill in the art that terms are used for the purpose of description and illustration, rather than that of limitation. Although the invention has been described with reference to particular means, materials and embodiments, the invention is not necessarily intended to be limited to the particulars disclosed; rather, the invention extends to all functionally equivalent structures, methods and uses as are within the scope of the appended claims.

The term "data repository" as used in applicant's disclosure shall also include any computer-readable storage medium and may also include solid state memory or packages housing one or more non-volatile read-only memories capable of storing, encoding or carrying a set or sets of instructions for execution by a computer processor or that cause a computer to perform any one or more of the operations disclosed herein. The disclosure is considered to include any computer-readable medium or other equivalent and successor media in which data and instructions may be stored.

The present disclosure also describes handheld and other computing devices and functions that may be implemented in particular embodiments with reference to particular standards or protocols, but it should be understood that the disclosure is not limited to any such standards or protocols. Standards and protocols referenced merely represent examples in the state of the art, and may be periodically superseded by replacement standards or protocols having the same or similar functions, and should be therefore considered equivalents thereof.

One or more embodiments of the disclosure may be referred to herein, individually or collectively, by the term "invention" merely for convenience and without intending to limit the scope of the present application to any particular invention or inventive concept. Although specific embodiments have been illustrated and described herein, it should be appreciated that any subsequent arrangement designed to achieve the same or similar purpose may be substituted for the specific embodiment(s) shown.

The above disclosed subject matter is to be considered illustrative, not restrictive, and the appended claims are intended to cover all modifications, enhancements and other embodiments which fall within the true scope and spirit of the invention as described and illustrated in the disclosure. Thus, the scope of the present disclosure is to be determined by the broadest permissible interpretation to the maximum extent allowed by law, of the following claims, and shall not be restricted or limited by the foregoing detailed description.

I claim:

1. A field-testing apparatus, comprising;
a first display facing in one direction, and a second display, separate from the first display, facing in a direction other than the facing direction of the first display, Internet communication functionality with at least one Internet-based computerized server, a local processor, on-board digital memory, and software executing on the local processor;
an accelerometer operating in the field-testing apparatus;
first and second graphic artifacts displayed on the first display, the first of which stays stationary on the first display, and the second of which moves in the first display in response to signals generated by the accelerometer; and
text instruction in the first display instructing a user to try to hold the apparatus to keep the second graphic artifact stationary relative to the first graphic artifact;
wherein the field-testing apparatus tracks and records movement of the second graphic artifact in the first display relative to the first graphic artifact, as an indication of balance.

2. The field-testing apparatus of claim 1 wherein the first display is a touchscreen, a third graphic artifact is displayed moving in the first display, text instruction is provided in the first display instructing the user to track the moving third graphic artifact with moving finger touch, and the field-testing apparatus generates data from the moving touch on the touchscreen as an indication of hand coordination.

3. The field-testing apparatus of claim 2, wherein the third graphic artifact is an S-curved line and the line is caused to snake back and forth in the touchscreen first display.

4. The field-testing apparatus of claim 3, wherein the third graphic artifact is caused to snake back and forth more rapidly as time passes.

5. The field-testing apparatus of claim 1 wherein additional graphic artifacts are displayed on the first display one-at-a-time and then removed, audio or text instructions are provided instructing the user to touch the additional graphic artifacts that appear, and the field-testing apparatus records finger touches that touch the additional graphic artifacts as indication of reaction time.

6. The field-testing apparatus of claim 5, wherein the field-testing apparatus detects and records touches that occur away from and outside predefined boundaries of the additional graphic artifacts that appear.

7. The field-testing apparatus of claim 6 wherein the field-testing apparatus determines a number of instances that a touch occurs away from and outside the predefined boundaries of the additional graphic artifacts and discontinues the test at a preset threshold of touches outside the predefined boundaries.

8. The field-testing apparatus of claim 1 further comprising an image capturing device facing away from the first display, wherein a moving pattern is presented on the first display, text instruction is displayed to follow the moving pattern with the eyes, and the image capturing device tracks eye movement responding to the moving pattern.

9. The field-testing apparatus of claim 1 further comprising a timer, wherein time devoted to interaction is recorded.

10. The field-testing apparatus of claim 1, wherein the first graphic artifact is a circle, the second graphic artifact is smaller than the circle, displayed initially within the circle, and the text instruction is to try to keep the second graphic artifact within the circle.

* * * * *